(12) United States Patent
Nunes et al.

(10) Patent No.: US 10,617,791 B2
(45) Date of Patent: Apr. 14, 2020

(54) INJECTABLE HYDROGELS FROM MICROFIBER SUSPENSIONS

(71) Applicant: TRUSTEES OF PRINCETON UNIVERSITY, Princeton, NJ (US)

(72) Inventors: Janine K. Nunes, Plainsboro, NJ (US); Antonio Perazzo, Ascea (IT); Stefano Guido, Naples (IT); Howard A. Stone, Princeton, NJ (US)

(73) Assignees: THE TRUSTEES OF PRINCETON UNIVERSITY, Princeton, NJ (US); UNIVERSITÀ DI NAPOLI "FEDERICO II" DIPARTIMENTO DI INGEGNERIA CHIMICA, DEI MATERIALI E DELLA PRODUZIONE INDUSTRIALE, Naples (IT)

( * ) Notice: Subject to any disclaimer, the term of this patent is extended or adjusted under 35 U.S.C. 154(b) by 0 days.

(21) Appl. No.: 15/169,010

(22) Filed: May 31, 2016

(65) Prior Publication Data

US 2016/0346427 A1 Dec. 1, 2016

Related U.S. Application Data

(60) Provisional application No. 62/168,402, filed on May 29, 2015.

(51) Int. Cl.
| | |
|---|---|
| *A61L 27/50* | (2006.01) |
| *A61L 27/52* | (2006.01) |
| *A61L 26/00* | (2006.01) |
| *A61L 27/54* | (2006.01) |
| *A61L 24/00* | (2006.01) |

(52) U.S. Cl.
CPC ............. *A61L 27/50* (2013.01); *A61L 24/001* (2013.01); *A61L 24/0015* (2013.01); *A61L 24/0031* (2013.01); *A61L 26/008* (2013.01); *A61L 26/0061* (2013.01); *A61L 26/0066* (2013.01); *A61L 27/52* (2013.01); *A61L 27/54* (2013.01); *A61L 2400/06* (2013.01)

(58) Field of Classification Search
CPC ........ A61L 27/50; A61L 27/52; A61L 26/008; A61L 26/006; A61L 27/54; A61L 24/0031; A61L 24/0015; A61L 24/001; A61L 26/0061; A61L 2400/06
See application file for complete search history.

(56) References Cited

FOREIGN PATENT DOCUMENTS

WO WO2011146296 * 11/2011

OTHER PUBLICATIONS

Zhu et al., "Bioactive modification of poly(ethylene glycol) hydrogels for tissue engineering", Biomaterials, 31(17), 2010, pp. 4639-4656.*

(Continued)

*Primary Examiner* — Trevor Love
(74) *Attorney, Agent, or Firm* — MH2 Technology Law Group, LLP

(57) ABSTRACT

Provided is a hydrogel. The hydrogel includes a liquid and a plurality of microfibers suspended in the liquid as an entangled network. The entangled network includes physically entangled microfibers that are mechanically interlocked.

21 Claims, 13 Drawing Sheets

(56) References Cited

OTHER PUBLICATIONS

Tong et al, Engineering interpenetrating network hydrogels as biomimetic cell niche with independently tunable biochemical and mechanical properties, 2013, Biomaterials, 35, pp. 1807-1815. (Year: 2013).*

Myung et al, Progress in the development of interpenetrating polymer network hydrogels, 2008, Polym Adv Technol, 19(6), pp. 647-657. (Year: 2008).*

Esibio, Pegda Vial, 1 mL, 2014, Biotime, Technical Data Sheet, 1 page. (Year: 2014).*

Daniele et al., "Microfluidic Strategies for Design and Assembly of Microfibers and Nanofibers with Tissue Engineering and Regenerative Medicine Applications," Adv. Healthcare Mater. 2014, pp. 1-18.

Marimuthu et al., "Spontaneouos Extrusion of Porous Amphiphilic Triblock Copolymeric Microfibers Under Microfluidic Conditions," Polymer Journal (2010), 42, pp. 100-102.

Nunes et al., "Control of the Length of Microfibers," Lab Chip, Dec. 2012, pp. 2301-2304.

Jun et al., "Microfluidic Spinning of Micro- and Nano-Scale Fibers for Tissue Engineering," Lab Chip, Jul. 2014, vol. 14, No. 13, pp. 2145-2160.

* cited by examiner

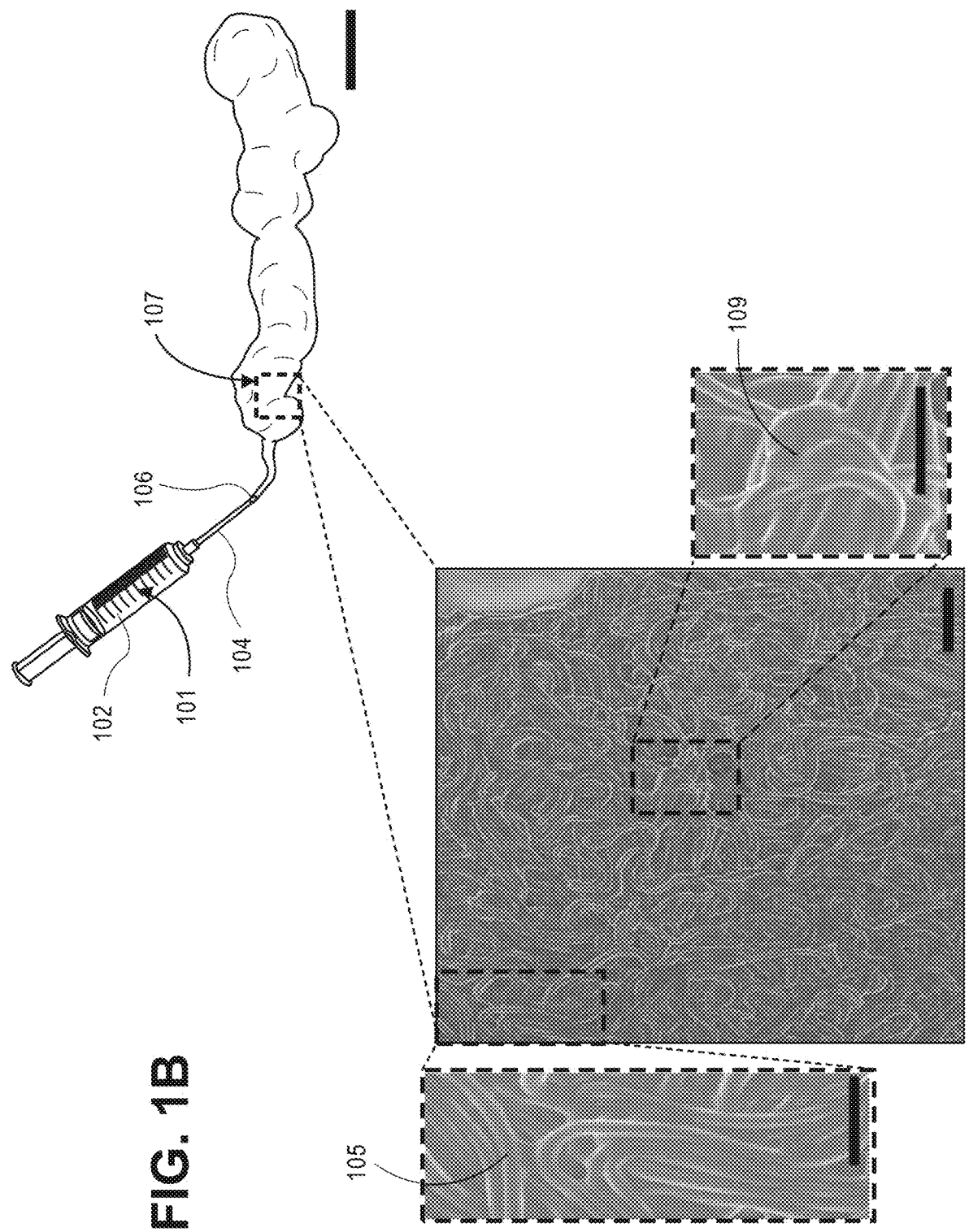

INJECTABLE HYDROGELS FROM MICROFIBER SUSPENSIONS

CROSS-REFERENCE TO RELATED APPLICATIONS

This application claims priority to U.S. Provisional Patent Application Ser. No. 62/168,402, filed May 29, 2015, the entirety of which is incorporated herein by reference.

FIELD

This disclosure is generally directed to hydrogels and methods of making hydrogels from flowable microfiber suspensions.

BACKGROUND

Hydrogels are among the most exploited materials in several applications, including tissue engineering, drug delivery, surgical adhesives and 3D bioprinting. There is growing interest in injectable hydrogels, especially as applied to surgical adhesives and bioprinting materials. Current methods for the in situ irreversible formation of hydrogels include chemical reactions, reversible polymer-particle interactions and physical associations, such as in the case of thermosensitive sol-gel reversible hydrogels. Methods of flow induced gelation have been previously reported, and they include flow induced gelation of micellar solutions, vortex induced gelation of protein solutions, and shear induced gelation of polymer-clay suspensions.

Meanwhile, microfibers are widely exploited in biomedical applications. A relevant feature of microfibers is that compounds, such as drugs, droplets, and biological materials, e.g., cells, can be readily encapsulated in their structure. Microfluidics provides the possibility to encapsulate compounds and manipulate the physical properties of a single fiber, such as Young modulus, aspect ratio (L/D, where L is length and D is the diameter of a fiber) and morphology. The microfibers can be dispersed in a liquid medium thus creating a suspension. Fiber suspensions are usually observed to behave as shear thinning fluids, i.e. the suspension viscosity decreases upon the action of flow, even when changing fiber size, aspect ratio, flexibility, or in the presence of noticeable normal stress differences. Shear thickening, where the viscosity increases with increasing shear rate, is rarely observed in flowing fiber suspensions, however it can be indicative of a gelation process. For example, shear thickening is observed with some polymer-particle suspensions, where the mechanism of gelation involves the bridging of particles with polymer chains. Another flow-induced gelling system is the flow-induced irreversible formation of nanogels from worm-like micelle solutions, which involves the rearrangement of the micelle structures to form junctions and branches that result in an entangled network. However, there are currently no processes or products that produce hydrogels in situ from flow induced gelation of microfibers, nor are there presently any products that use microfibers to form hydrogel materials.

Improved hydrogels and methods for producing hydrogels, beyond the synthetic and physical approaches that are currently available, would provide for new and emerging applications and would be a welcome addition to the art.

SUMMARY

As used herein, the terms "chemical crosslinking", "chemically crosslinked" and variations thereof refer to the formation or existence of irreversible, covalent bonds between two or more polymer backbones. As used herein, the term "mechanical interlocking," "mechanically interlocked" and variations thereof refer to the formation or existence of at least one irreversible knot formed between two or more sections of a single, discrete fiber or at least one knot formed between two or more single, discrete fibers. As used herein, the terms "physically entangled," "physical entanglements," "physically entangling" and variations thereof refer to the formation or existence of an interlacement, including mechanical interlocking, between flexible, discrete fibers. As used herein, the term "irreversible" means that an object retains its mechanical properties even when a stress applied during its formation is removed.

In an embodiment, there is a hydrogel comprising: a liquid; and a plurality of microfibers suspended in the liquid as an entangled network, wherein the entangled network comprises physically entangled microfibers that are mechanically interlocked.

In another embodiment, there is a method of forming a hydrogel, comprising: providing a flowable suspension comprised of a plurality of microfibers disposed in a liquid carrier, wherein the flowable suspension is a shear thickening fluid; physically entangling the plurality of fibers by extruding the flowable suspension through an open end of a conduit; and forming the hydrogel by mechanically interlocking the plurality of microfibers.

In yet another embodiment, there is a biocompatible material comprising: a shear thickening fluid, the shear thickening fluid comprising, a liquid, and a plurality of hydrophilic microfibers suspended in the liquid, wherein the plurality of microfibers encapsulate a therapeutic, and wherein the hydrophilic microfibers have an aspect ratio of about 200 to about 10,000.

In an additional method, there is a hydrogel comprising: a liquid; and a plurality of physically entangled fibers disposed in the liquid. The physically entangled fibers are formed by: providing a flowable suspension comprised of a plurality of fibers disposed in the liquid; and mechanically interlocking the plurality of fibers by extruding the suspension through an open end of a conduit.

Advantages of the embodiments will be set forth in part in the description which follows, and in part will be understood from the description, or may be learned by practice of the invention. The advantages will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate embodiments of the invention and together with the description, serve to explain the principles of the invention.

BRIEF DESCRIPTION OF THE DRAWINGS

FIG. 1B illustrates transforming the flowable suspension of FIG. 1A into a hydrogel according to a method of an embodiment. The inset is an SEM image of dried hydrogel, with further magnified inset images showing different regions of the hydrogel. Scale bars represent 200 μm in the low magnification image (larger inset) and 100 μm in higher magnification inset images (to the left and right).

FIG. 7A is an image of an as-extruded fiber hydrogel and FIG. 7B is an image of the same hydrogel of FIG. 7A, but shown swollen a minute after a few drops of water were added thereto. Scale bars in FIGS. 7A-7B represent 2 mm.

FIG. 7C is an image showing microscopic detail of the as-extruded fiber hydrogel of FIG. 7A and FIG. 7D is an image showing microscopic detail of the swollen hydrogel of FIG. 7B. Scale bars in FIGS. 7C-7D represent 200 μm.

DETAILED DESCRIPTION OF THE EMBODIMENTS

Figure 1A:
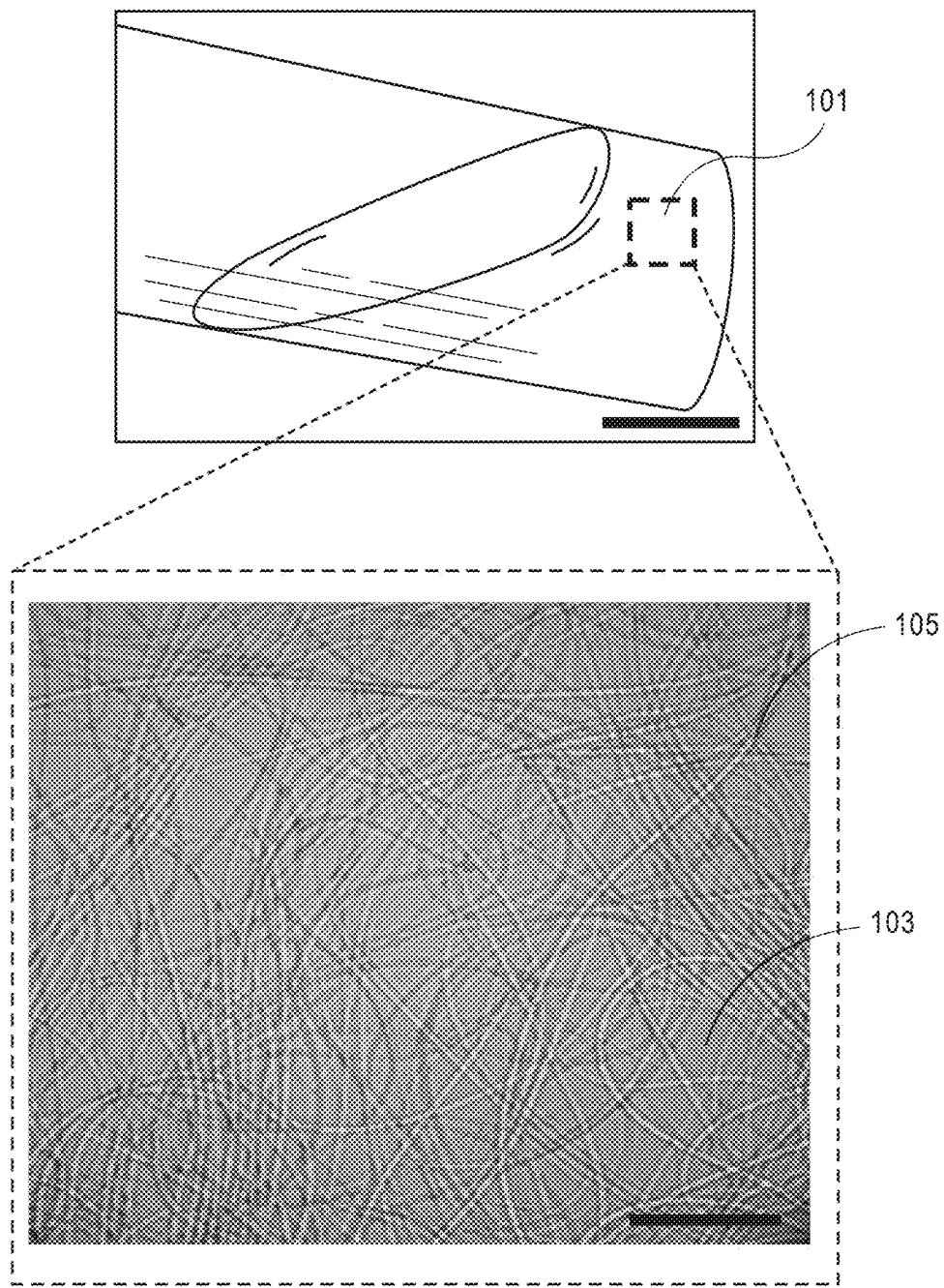
FIG. 1A illustrates a flowable suspension of the embodiments according to an embodiment. The flowable suspension is shown flowing within a tilted vial. The inset is an SEM image of a fiber suspension shows that the flowable suspension is non-sheared and a plurality of flexible microfibers (by virtue of their highly bent conformations) with a scale bar representing about 500 µm.

Reference will now be made in detail to the present embodiments, examples of which are illustrated in the accompanying drawings. Wherever possible, the same reference numbers will be used throughout the drawings to refer to the same or like parts.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less that 10" can assume negative values, e.g. −1, −2, −3, −10, −20, −30, etc.

The following embodiments are described for illustrative purposes only with reference to the figures. Those of skill in the art will appreciate that the following description is exemplary in nature, and that various modifications to the parameters set forth herein could be made without departing from the scope of the present invention. It is intended that the specification and examples be considered as examples only. The various embodiments are not necessarily mutually exclusive, as some embodiments can be combined with one or more other embodiments to form new embodiments.

Disclosed herein is a suspension of highly flexible microfibers obtained by microfluidic or other methods that can be converted to a hydrogel by flow-induced gelation without any further chemical cross-linking. Gelation is elicited by the formation of flow induced irreversible entanglements of the microfibers. A significant consequence of these properties is that the suspension is injectable by a syringe and comes out of the needle directly as a hydrogel with no need of further treatments. This feature makes the microfiber suspension a promising material for scaffold fabrication in situ in biomedical applications, and also for home and personal care products. More particularly, disclosed is the formation of a hydrogel from a suspension of flexible hydrophilic microfibers when subjected to stress induced by flow. The disclosed approach does not use chemical reactions to gel the suspension; it is simply an irreversible mechanical process, which is advantageous for in vitro and in vivo applications where you would want to minimize the presence of chemicals that may not be compatible with cells or other biomaterials.

Also described herein are hydrogel compositions and methods of making such hydrogels. The hydrogels may be formed by processes that include physical entanglements of, for example, flexible microfibers having very high aspect ratios, in which the entanglements are induced by flow. This general mechanical approach provides for an observable shear thickening—a clear signature of fiber entanglements—which leads to gelation of microfiber suspensions. While not limited to any particular theory, it is believed that such shear thickening is the result of flow-induced mechanical entanglements of individual fiber strands, owing to their high aspect ratio, flexibility and that the entanglements are not due to chemical or intermolecular interactions. Thus, a conversion from a microfiber suspension into a hydrogel is induced by subjecting the microfibers to stress, which leads to the formation of a porous entangled network of microfibers. In an example, such a stress is provided via the extrusion of such suspensions from a needle and syringe.

In FIG. 1A a flowable suspension 101 is provided, for example, in a container. The flowable suspension may be comprised of a plurality of microfibers 105 disposed in a liquid carrier 103. The flowable suspension may be configured with a preselected volume fraction ($\phi$) of the microfibers 105 in the liquid carrier. The microfibers 105 are selected to have flexibility, as evidenced by the inset in FIG. 1A showing bends along the length of the microfibers. The flexibility not only allows the microfibers to remain in suspension when no stress is applied, but to also form entangled networks when sufficient stress is applied. In an embodiment, the flowable suspension comprises a fiber volume fraction in the range of from about $\phi=0.2$ to about $\phi=0.4$.

As shown in FIG. 1B, the flowable suspension may be exposed to a stress, for example, a flow-induced stress, to form a hydrogel 107. In an embodiment, the flow-induced stress may be applied by extruding the flowable suspension 101 through and out of conduit. During the extrusion of the hydrogel 107, a network of fiber entanglements (i.e., an entangled network) are created. Such entanglements may be irreversibly formed. Fibers need a stress to become entangled and such a stress can be provided by the action of flow. A pressure-driven flow can be provided by extrusion from a first chamber having a first cross-sectional area and through a conduit having a second cross-sectional area that is smaller than the first cross-sectional area. As a result, the flow may be characterized in a first regime as Poiseuille flow in the region of the first chamber (e.g., a syringe having a diameter greater than about 10 mm) having the constant cross-sectional area. The flow may be characterized in a second regime as extensional flow brought about by the abrupt change of cross sectional area when the suspension flows from the first chamber into the conduit (e.g., a needle having a diameter from about 0.1 mm to about 1 mm). While not limited to any particular theory, it is believed that extensional flow, along with Poiseuille flow within the needle, plays a key role in hydrogel formation. The former is able to cause rapid local elongation and induce a stress proportional to the abrupt fluid velocity change due to the passage from a larger section into a smaller one, whereas the latter, given the small diameter of the needle, is able to keep the fibers confined as well as provide a stress proportional to the velocity gradient along the needle cross-sectional area, thus promoting fiber entanglements. As the hydrogel is formed from the flowable suspension, some of the liquid carrier is "squeezed out" as the material flows through the conduit, for example, as it exits an opening of the conduit. As a result, although some of the liquid carrier remains in the hydrogel along with the entangled network of fibers, the effective concentration of fibers in the hydrogel increases relative to the concentration in the solution. Accordingly, in an embodiment, the hydrogel comprises a fiber volume fraction in the range of from about $\phi=0.4$ to about $\phi=0.8$.

In an implementation, therefore, as shown in FIG. 1B, the flowable suspension 101 may be provided in a first chamber in a syringe 102, and pressure may be applied against the syringe's plunger to flow the flowable suspension through the open end of a conduit, such as a open end 106 of needle 104. As a result, at least some of the microfibers 105 may form entangled networks 109 comprising physically entangled microfibers that are not chemically crosslinked to each other. While not limited to any particular theory, it is believed that the forming of such entangled networks leads to the macroscopic gelation of the flowable suspension, when it is subjected to strong shear and extensional flows such as those produced during extrusion from a needle.

Accordingly, a mechanical approach for forming hydrogels is disclosed in that the plurality of microfibers 105 in the suspension 101 become mechanically interlocked. In an embodiment, the plurality of microfibers are not covalently cross-linked to one another. In other words, a physical entanglement of the fibers in the embodiments described herein is independent of chemical reactions or restructuring of individual components in the flowable solution. While not limited to any particular theory, it is believed that such mechanical cross-linking depends primarily on the microfiber aspect ratio, flexibility, concentration and stress induced by flow.

Figure 1C:
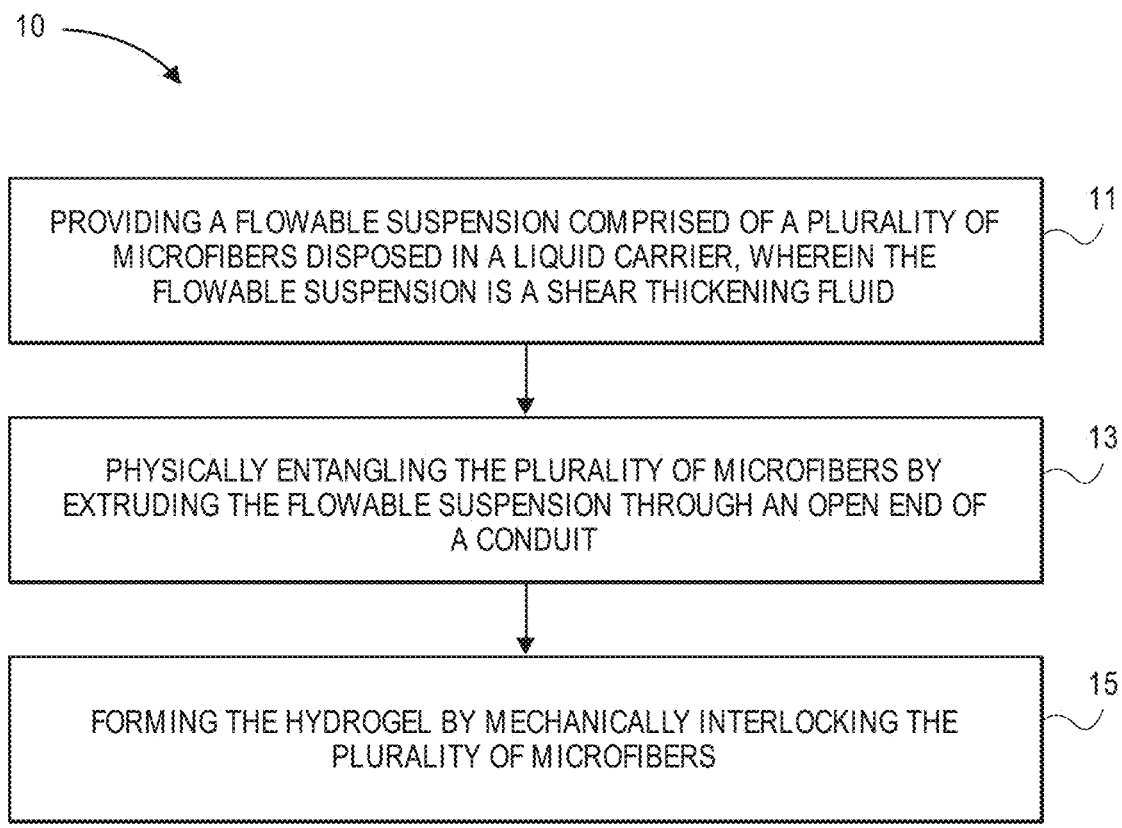
FIG. 1C is a flowchart illustrating a method of forming a hydrogel.

Accordingly, as shown in FIG. 1C, in an embodiment there is a method 10 for forming a hydrogel. The method can include a step 11 of providing a flowable suspension comprised of a plurality of microfibers disposed in a liquid carrier. The flowable suspension can be a shear thickening fluid. The method can also include a step 13 of mechanically entangling the plurality of microfibers by extruding the flowable suspension through an open end of the conduit. The method can also include a step 15 of forming the hydrogel by mechanically interlocking the plurality of microfibers. In an embodiment, the hydrogel is formed without covalently cross-linking the plurality of microfibers. More generally, the steps for forming the disclosed hydrogel comprise making flexible fibers by a method producing long, thin and flexible fibers, and taking a suspension of the fibers and flowing them through a channel and out of a nozzle or another extrusion device—it is this flow-induced gelation that produces a gel of entangled fibers. As disclosed, the hydrogels result from a combination of i) suspensions of long and flexible fibers prepared by microfluidics or other methods and ii) appropriate flow conditions, capable of both entangling the fibers and squeezing out the solvent therein, that result from the aforementioned extrusion geometries (or other approaches including confined compression with a porous filter, elongational flow, squeezing flow, and their combinations).

Figure 8:
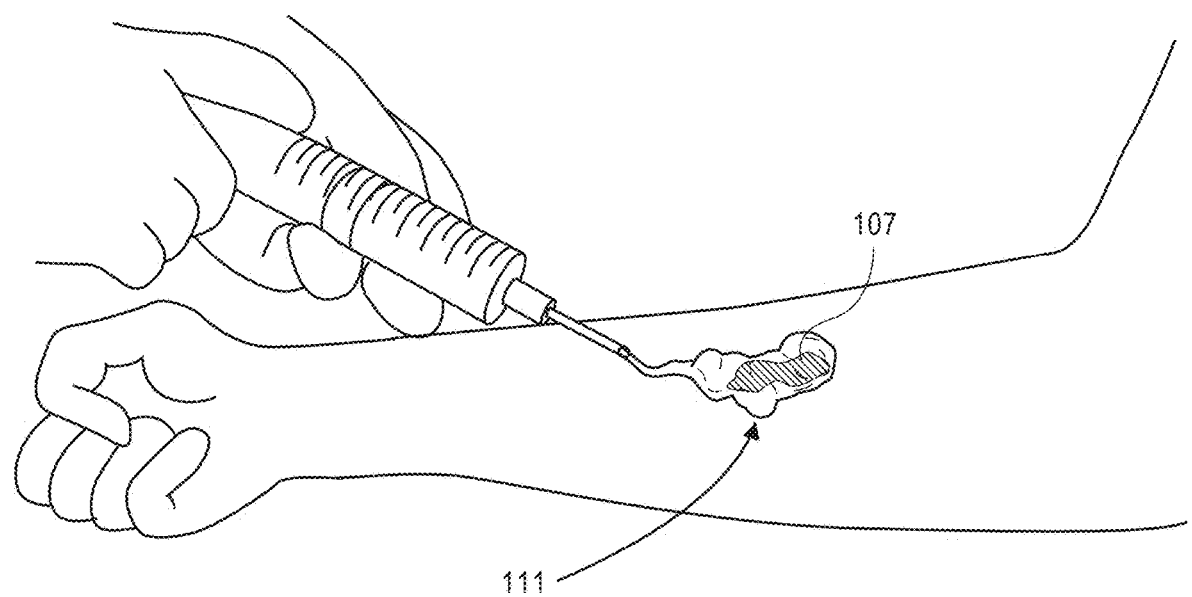
FIG. 8 illustrates use of an embodiment of a hydrogel as a wound dressing.
Figure 9:
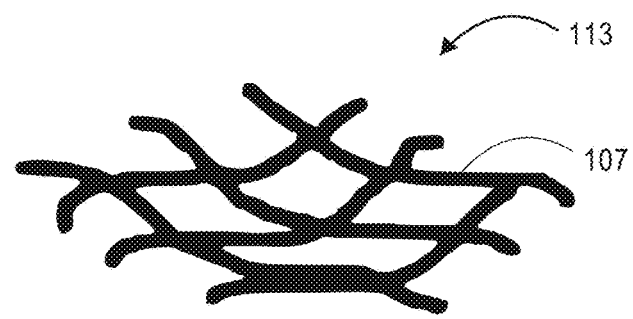
FIG. 9 illustrates use of an embodiment of a hydrogel as scaffolding.
Figure 10:
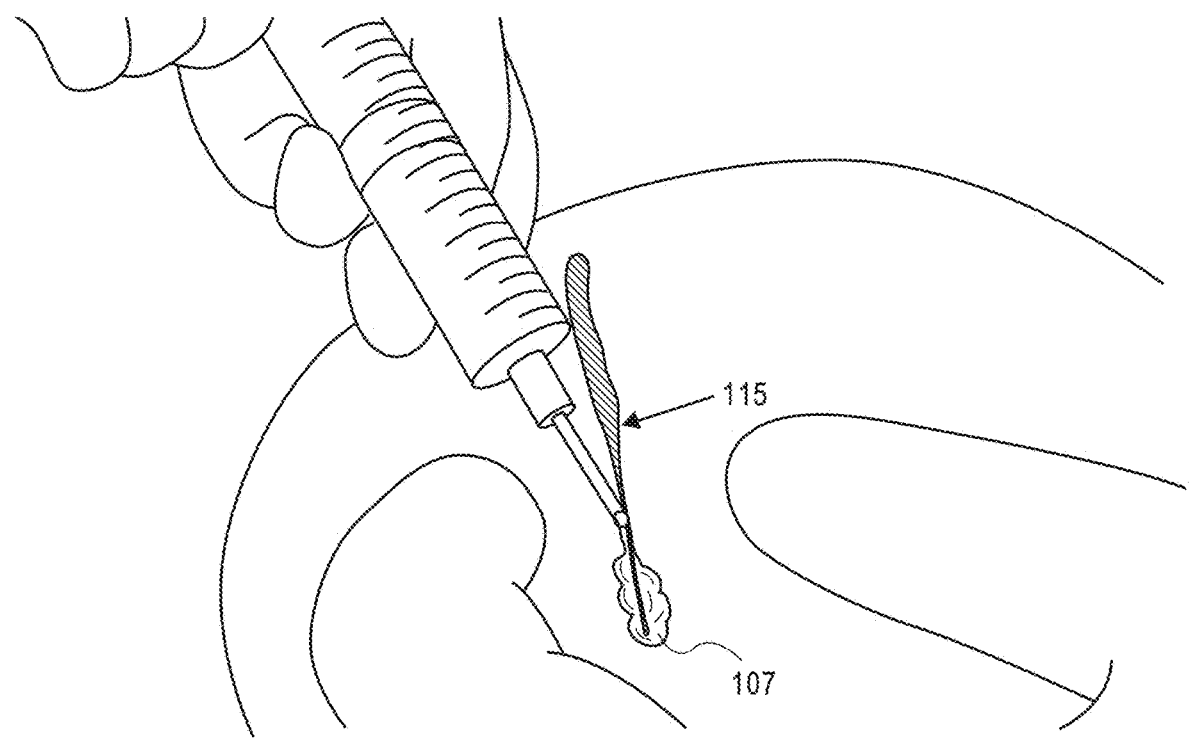
FIG. 10 illustrates use of an embodiment of a hydrogel as surgical adhesive.
Figure 11:
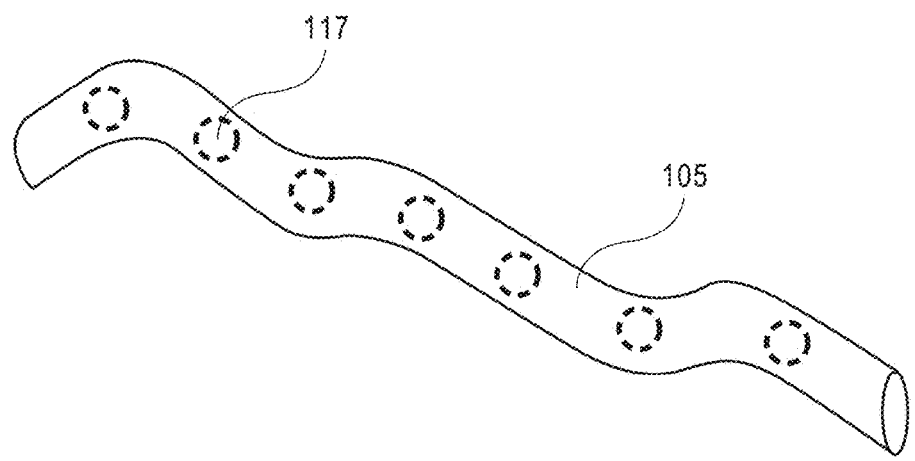
FIG. 11 is an illustration of a microfiber that encapsulates cargo according to an embodiment.

Injectable hydrogels are attractive for many in vivo applications, where hydrogels need to be delivered in a minimally invasive manner. Accordingly, in some embodiments, a biocompatible material comprises a shear thickening fluid. The shear thickening fluid can comprise a liquid and a plurality of microfibers suspended in the liquid. In other words, such a shear thickening fluid may be the suspension 101 described above. Upon in vivo extrusion through a conduit, such as needle 104, the shear thickening liquid forms a hydrogel 107. Such a biocompatible material may be used as a wound dressing 115 (FIG. 8), scaffolding 113 (FIG. 9), or a surgical adhesive 115 (FIG. 11). In an embodiment, hydrogels formed from such biocompatible materials may be used as injectable hydrogels.

Additionally, a desirable property of injectable hydrogels is shear thinning behavior. In an embodiment, therefore, hydrogel formation in a microfiber suspension as described above is initiated by mechanically entangling of the plurality of microfibers, for example, by extruding the flowable suspension through an open end of a conduit, such as a needle. Such hydrogels of the embodiments exhibit shear thinning behavior as described in the examples below. That is, the effective viscosity, or resistance to flow, decreases as it is exposed to higher shear stresses.

It is noted that mechanical properties of a material may be characterized, in part, by relative viscosity and elasticity of the materials. With respect to elasticity, the material shear elastic modulus (G') may be considered, and with respect to viscosity, a material's viscous modulus (G") may be considered. A mechanical/rheological signature of gels is that G'>>G" (with both independent from the frequency of deformation). Accordingly, a hydrogel according to an embodiment may comprise a shear elastic modulus, G', and a viscous modulus G", wherein G' is greater than G".

Microfibers

Microfibers of the embodiments are not necessarily limited by any particular constraint except that they should be in a flexible regime. Flexibility can be described by the effective stiffness ($S^{eff}$). Generally, for $S^{eff} \ll 1$, fibers are flexible, whereas for large values of $S^{eff}$, fibers are classified as rigid. In an embodiment, each of the plurality of microfibers comprise a maximum $S^{eff}$ of less than one, including a value of $S^{eff}$ in a range of from about $10^{-6}$ to about $10^{-3}$, such as $10^{-5}$ to $10^{-3}$, for example, a value of about $3.67 \times 10^{-4}$, wherein $S^{eff}$ is calculated by, $$S^{eff} = \frac{E_Y \pi D^4}{64 \eta_m \dot{\gamma} L^4}$$

where $E_Y$ is Young's modulus, L is fiber length, D is fiber diameter, $\eta_m$ is a viscosity of a flowable suspension prior to shear flow to physically entangle the microfibers, and $\dot{\gamma}$ a shear rate. In an example, $\dot{\gamma}$ ranges from about 1 s$^{-1}$ to about 100 s$^{-1}$, but $\dot{\gamma}$ need not be limited to values in this range.

The microfibers of the embodiments can be fabricated such that their properties including, for example, modulus, aspect ratio, morphology, composition, can be tailored with a high degree of control. The microfibers may be formed via a microfluidic method, a wet spinning method or an electrospinning method. In one example, microfluidic methods may be used to produce microfibers having uniform dimensions. As a result, suspensions of nearly monodisperse, high aspect ratio, and/or flexible microfibers can be manufactured.

The diameter and length of the microfibers can be controlled in situ during their fabrication. In one method, the diameter and length of the microfibers can be controlled using, for example, pulsed ultraviolet light and a photoreactive fiber solution. It is noted that although the dimensions of the microfibers are not necessarily limited, such parameters should be selected such that the microfibers do not accumulate to cause clogging as they flow through a conduit during the entangling process described above.

In an embodiment, the plurality of microfibers of the embodiments may each comprise an aspect ratio, where the aspect ratio is defined by a length (L) of a fiber, divided by diameter (D) of a fiber. That is, aspect ratio=L/D. An aspect ratio of the microfibers may comprise a value in a range from about 200 to about 10,000, such as from about 250 to about 5000, for example, from about 300 to about 350. In one example, each of the plurality of microfibers comprise aspect ratios of about 340. In one example, a length of the microfibers may be greater than a diameter of the microfibers.

In an embodiment, each of the plurality of microfibers may comprise lengths in the range of from about 1 mm to about 50 mm, such as from about 5 mm to about 30 mm, for example, from about 10 mm to about 15 mm. In one example, each of the plurality of fibers comprise lengths of about 12 mm.

In an embodiment, each of the plurality of microfibers may comprise diameters in the range of from about 0.5 μm to about 1500 μm, such as from about 1 μm to about 1000 μm, for example, from about 20 μm to about 40 μm. In one example, each of the plurality of fibers comprise diameters of about 35 μm.

Compositions of the microfibers may be tailored for particular needs. Compositions of the microfibers may include one or more of polyurethane acrylate (PUA), gelatin-hydroxyphenylpropionic acid (Gtn-HPA), 4-hydroxybutyl acrylate (4-HBA), poly(ethylene glycol) diacrylate (PEG-DA), poly(ethylene glycol) dimethacrylate (PEG-DMA), alginate, polylysine (PLL), poly(lactic-co-glycolic acid) (PLGA), amphiphilic triblock poly(p-dioxanone-co-caprolactone)-block-poly(ethylene oxide)-block-poly(p-dioxanone-co-caprolactone) (PPDO-co-PCL-b-PEG-b-PPDO-co-PCL), polybenzimidazole (PBI), regenerated silk fibroin (RSF), collagen, poly-(N-isopropyl acrylamide) (poly(NIPAAM)), poly(sulfone) (PSF), polyacrylonitrile) (PSF), polystyrene (PS), fibrin, polyurethane (PU), poly(methylmethacrylate) (PMMA), vanadium pentoxide ($V_2O_5$), or mixtures thereof. In one example, compositions of the microfibers may include alginate with one or more of collagen, fibrin, agarose, or mixtures thereof. In an embodiment, each of the microfibers may comprise crosslinked polymers.

Generally, the microfibers of the embodiments may be characterized as solvophilic. For example, the microfibers of the embodiments may be hydrophilic. However, the embodiments are not so limited and the microfibers may be hydrophobic.

The microfibers may be biocompatible and suitable for tissue engineering applications. For example, fiber hydrogels of the embodiments comprise adhesive properties that provide for in vivo applications. That is, a concentrated suspension of the microfibers undergoes irreversible gelation using a simple mechanical process that does not use chemical reactions. The fiber hydrogel exhibits typical properties of a gel: the mechanical properties are consistent with that of a soft viscoelastic solid and it swells in water. The hydrogel forms in situ, so it can be used as an injectable hydrogel, where it forms immediately upon extrusion from a needle (or another extrusion device such as a slit, a pore, an array of pores, an array of needles, etc.) and the disclosed injectable hydrogels from microfiber suspensions can be employed, inter alia, for the in situ generation of substrates for cells in tissue engineering, as a drug delivery material, and in wound dressings. Other biomedical applications include a surgical sealant and high strength adhesive; a support for nerve regeneration; and a cartilage replacement, among many others.

In an embodiment, the microfibers may be selected such that the flowable suspension is non-Brownian. It is noted that the Peclet (Pe) number compares hydrodynamic forces versus Brownian forces and may be used to discriminate between Brownian and non-Brownian suspensions, where Pe can be estimated from:

$$Pe = \frac{\eta_m \dot{\gamma} \pi L^3}{3 k_B T \ln\left(\frac{L}{D}\right)}$$

Where L and D are fiber length and diameter, respectively, $\beta_m$ the medium viscosity $\dot{\gamma}$, the shear rate, $k_B$ the Boltzmann constant and T the absolute temperature. Fiber suspensions are considered Non-Brownian at high values of Pe. Accordingly, in an embodiment, the flowable suspensions of the embodiments may comprise a value for Pe greater than about $10^8$. It is noted that the Pe number for flowable suspensions of the embodiments has been calculated to be about $10^{11}$ at the lowest shear rate of 1 s$^{-1}$.

In an embodiment, at least one of the plurality of microfibers 105 may encapsulate a cargo 117 (FIG. 11). That is, the microfibers themselves can be prepared with encapsulated cargos. The cargo may comprise one or more of therapeutics, biological materials or sensing materials. For example, drugs such as protein therapeutics (e.g., hydrophobic drug compounds, antibiotics), biological materials such as living cells, sensing materials (e.g., fluorescent, magnetic, and/or metal nanoparticles) and droplets, may be loaded into microfibers during production, for example, as prepared using known microfluidic technologies. Furthermore, the release of these cargo materials can be tailored according to the specific chemistry and crosslink density in the microfibers (i.e., the crosslink density of polymers formed during synthesis of the individual fibers).

As described above, in an embodiment, each of the microfibers may comprise a polymer. Further, the polymer may have at least one charged group that may be functionalized, for example, after gelation of the suspension. In an example, the microfibers may be functionalized with at least one protein.

As discussed, the microfibers can be made using any method that can produce very flexible high aspect ratio hydrophilic fibers, and the fibers should have suitable mechanical properties, water-loving characteristics, and should be able to be made into concentrated suspensions. Employing microfluidics as the method to make them has the advantage that there are strategies for controlling many of the properties of the fibers very well, and other methods are continuous, so the fibers may have to be cut to the appropriate length after production Liquid Carrier The fibers may be suspended in a liquid carrier, for example, at a predetermined volume fraction prior to gelation. Even after gelation, the hydrogels of the embodiments may still include the liquid, although some of the liquid may be removed upon transforming the microfiber solution into the hydrogel, for example, according to methods described herein. The liquid may include at least one solute to "density match" with the microfibers, leading to a reduction or elimination of microfiber settling. The liquid may include at least one surfactant, leading to a reduction or elimination of microfiber sticking. Therefore, in some embodiments, the liquid may comprise at least one solvent, such as water, and may include at least one solute such as a salt and/or at least one solution modifier such as a surfactant. In an embodiment, the liquid comprises water alone. In an embodiment, the liquid comprises an aqueous solution comprised of at least water and at least one solute and/or at least one surfactant. In an embodiment, the liquid comprises a polymer solution (e.g., a polymer aqueous solution). Polymer aqueous solutions may include at least one polymer such as poly(ethylene glycol), and proteins such as albumin. In an embodiment, the fibers may be suspended in a cell growth medium or phosphate buffered saline (PBS).

Solutes may include salts selected from one or more of sodium chloride, cesium chloride, potassium chloride, potassium dihydrogen phosphate, sodium hydrogen phosphate, or combinations thereof.

Solution modifiers may be selected from pluronics, surfactants or both. Surfactants may be selected from at least one surfactant, such as at least one nonionic surfactant, including TWEEN® 80 or TWEEN® 20 non-ionic surfactant solutions available from Sigma-Aldrich Co. LLC of St. Louis, Mo.

In the method of the disclosed approach, a suspension of flexible hydrophilic microfibers is subjected to stress induced by flow, which immediately forms an entangled network filled with water, i.e. a hydrogel. For example, the suspension can be extruded from a needle (or another extrusion device such as a slit, a pore, an array of pores, an array of needles, etc.) to form the hydrogel.

While the disclosed approach for forming hydrogels may call for concentrated suspensions of high aspect ratio flexible microfibers, which requires careful handling to prevent excessive entanglements and gelation prematurely, the suspensions flow and can be processed below a critical stress.

EXAMPLES

Example 1A—Microfluidic Synthesis of Fibers

Microfluidic channels were prepared using standard methods of soft lithography. Polydimethylsiloxane (PDMS; available as SYLGARD® 184 from Dow Corning Corp. of Auburn, Mich. and may be purchased from Ellsworth Corporation of Germantown, Wis.) channels were plasma-bonded to PDMS-coated glass slides using a Corona Surface Treater (Electro-Technic Products, Inc.). The microfluidic device had two inlets, one for the oil continuous phase and the other for an oligomer solution. The individual liquid phases met at a hydrodynamic focusing region where a cylindrical oligomer jet formed. The jet, sheathed by the continuous phase, flowed through a main channel of width=200 μm and height=50 μm. The oil continuous phase was composed of 60 vol % heavy mineral oil (Fisher Scientific), 30 vol % hexadecane and 10 vol % SPAN® 80 nonionic surfactant. The oligomer solution was composed of 54 vol % poly(ethylene glycol) diacrylate (PEG-DA; MW=575 g/mol), 42 vol % de-ionized (DI) water and 4 vol % 2-hydroxy-2-methylpropiophenone. The oil and PEG-DA phases were pumped at constant flow rates of 1.2 mL/hr and 0.16 mL/hr, respectively, using syringe pumps (KD Scientific and Harvard Apparatus). Unless otherwise stated, all chemicals were purchased from Sigma-Aldrich.

Ultraviolet (UV) light was used to initiate the crosslinking reaction in the monomer jet. The UV light was supplied by the fluorescence light source (120 W mercury short arc lamp) on a Leica DMI4000B inverted microscope via the 20× magnification objective lens. No filters were used to modify the spectrum of light supplied from the lamp, thus the light incident on the PEG-DA jet was not monochromatic. UV light intensity was measured at the bottom surface of the device to be in the range 18-20 mW/cm$^2$ for all presented results. The length of the fibers was controlled optically by pulsing the UV light incident on the monomer jet. The shutter was programmed to open for 370 ms and close for 630 ms for a specified number of cycles, depending on the desired suspension concentration.

The fibers were collected in DI water and washed 3 times in 1 wt % TWEEN® 80 solution, followed by at least 2 washes in 0.1 wt % TWEEN® 80 solution. For rheology measurements, the fibers were re-suspended in an aqueous solution containing 0.1 wt % TWEEN® 80 and 12 wt % CsCl to avoid interfiber sticking and fiber settling.

Example 1B—Characterization of the Physical Properties of the Fibers

Lengths of fibers from Example 1A were measured. The lengths were measured by capturing images while flowing the fibers through long serpentine microchannels. Fiber lengths and diameters were taken as the average length and diameter of approximately 100 different fibers as measured using ImageJ software (ImageJ version 1.44p, NIH, Bethesda, Md., USA): length=11.76±0.52 mm, diameter=35.3±3.4 µm. The Young's modulus, $E_Y$, was estimated to be ~$10^5$ Pa, based on previously reported small amplitude oscillatory measurements of the shear moduli, G' and G", of bulk cross-linked PEG-DA hydrogels (of the same molecular weight used here) using an Anton Paar MCR 501 Rheometer, given that G*=G'+iG" and $E_Y$=2G*(1+v), where v is the Poisson ratio and can range from ~0.25-0.4 for hydrogels depending on the degree of cross-linking.

Scanning electron microscopy images of the fibers in the dried hydrogel were captured on a Quanta 200 FE-ESEM, in low vacuum mode.

Example 1C—Rheological Measurements

The rheological properties of fiber suspensions were measured using a stress-controlled rheometer (Physica MCR 301, available from Anton Paar Instruments of Austria). All of the rheometry experiments were carried out at 23° C. Usually, in rotational rheometry, a cone-plate geometry is exploited in order to obtain a homogeneous velocity gradient throughout the sample. Nevertheless, in the cone and plate geometry the gap size at the cone tip is fixed around 50 µm thus confining the fibers, i.e., the fiber diameter is comparable with the gap. In the latter case, undesired wall effects act to induce faster fiber orientation compared to the unconfined case. Hence, the parallel-plate geometry, where the gap can be varied, is commonly adopted for non-Brownian suspension rheometry and so a parallel-plate geometry was used in order to reduce wall effects. To minimize the wall slip effect, a parallel plate geometry with a roughness, Ra=6-7 µm, and a plate diameter of 75 mm was used. However, as a comparison, measurements were conducted with a smooth plate geometry having a plate diameter of 50 mm. The gap was fixed at 0.75 mm in the smooth geometry and 0.70 mm in the rough apparatus as it was not possible to contain a water-based suspension between the plates for higher gap size.

Figure 2A:
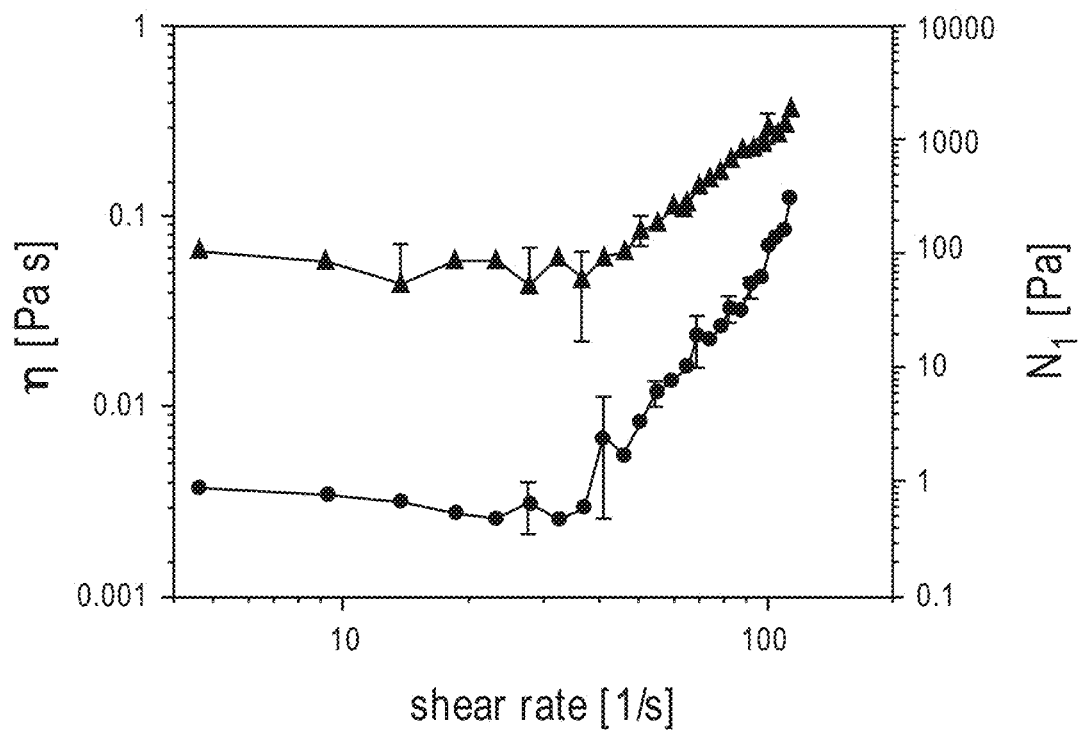
FIGS. 2A-2C are flow where viscosity η and first normal stress difference $N_1$ are plotted as a function of shear rate for microfiber suspensions at microfiber volume fractions (ϕ) of ϕ=0.07, ϕ=0.1 and ϕ=0.2.
Figure 2B:
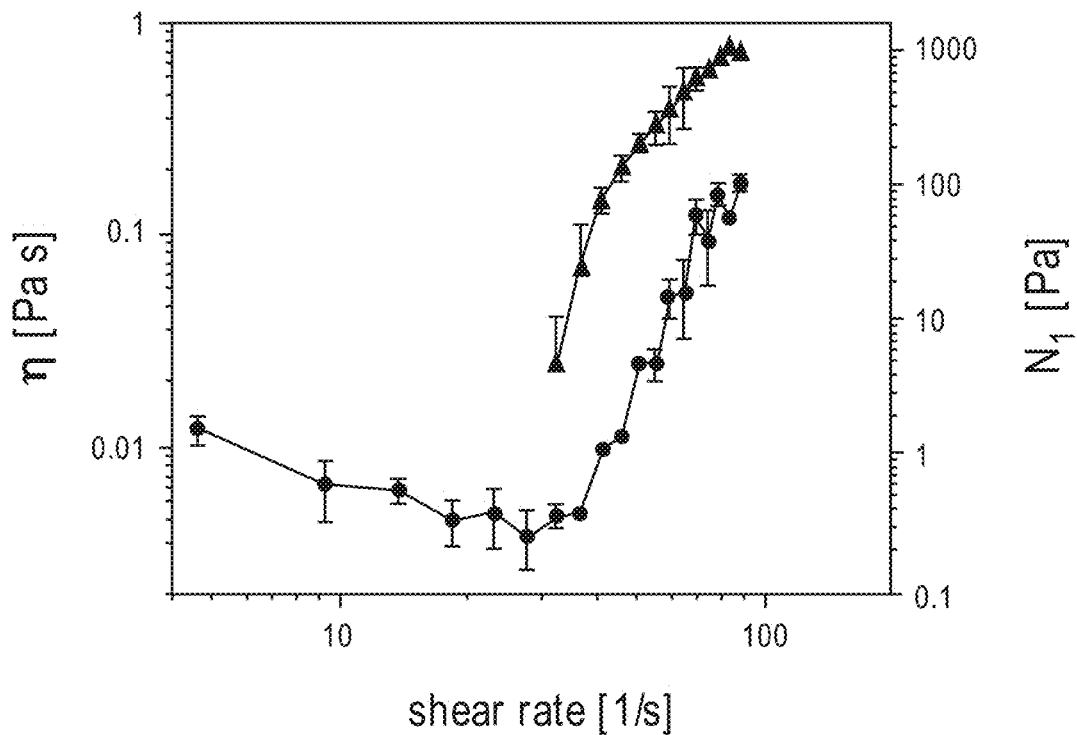
Figure 2C:
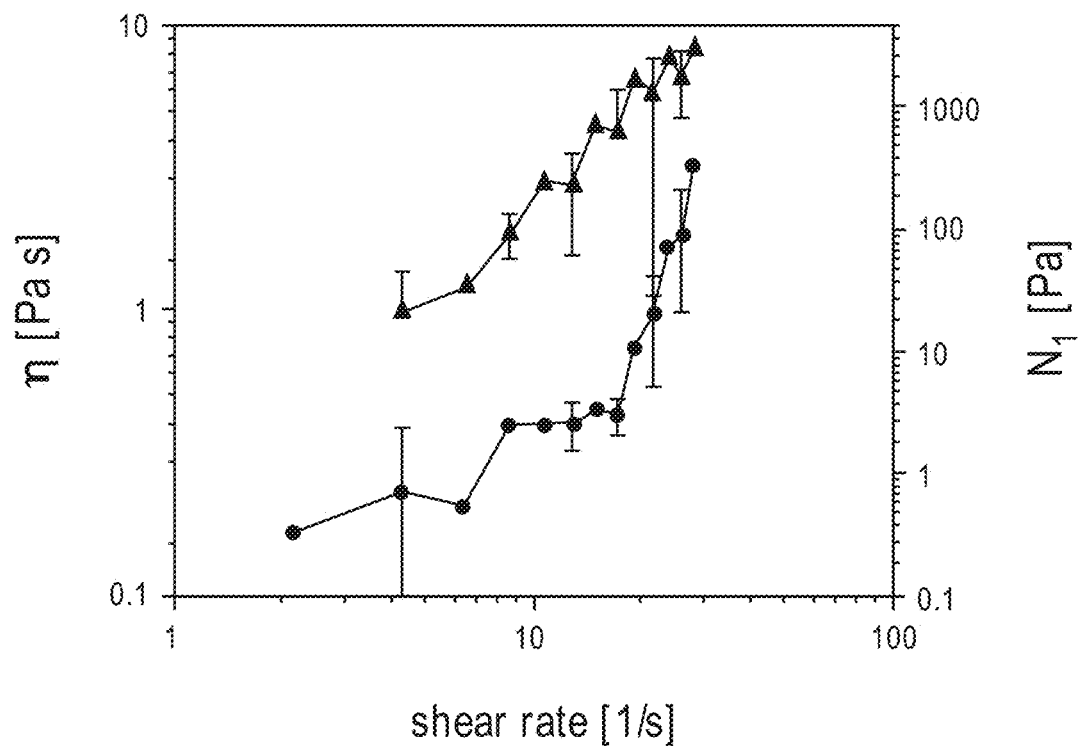
Figure 2D:
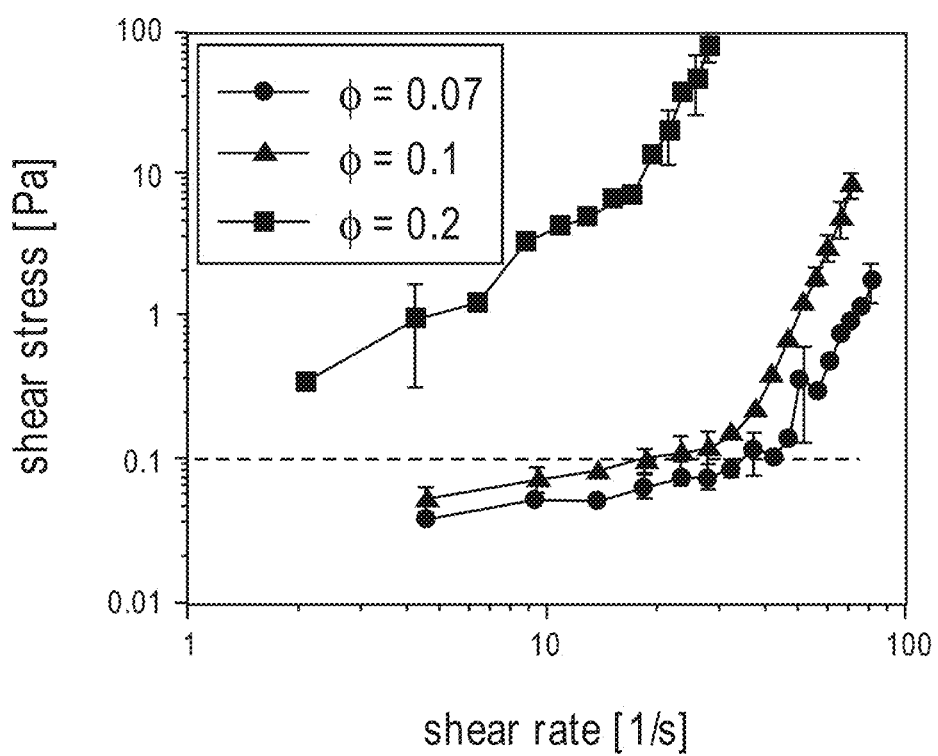
FIG. 2D is a shear stress plot for fiber suspensions at various fiber volume fractions.

To gain some understanding of the network formation in the microfiber suspensions, viscosity, η, and first normal stress difference, $N_1$, of the suspensions were measured as a function of the shear rate, $\dot{\gamma}$, for different volume fractions of fibers. FIGS. 2A-2C show the flow curves of the fiber suspensions at three different volume fractions φ=0.07, φ=1 and φ=0.2. As shown, fiber suspensions exhibit an initial shear thinning that increases with increasing fiber content. Furthermore, the zero shear viscosity also increases as fiber concentration increases. One significant rheological feature of these fiber suspensions is the presence of shear thickening over a significant range of shear rates, which follows the shear thinning regime. The onset of shear thickening for different concentrations can be more clearly observed in the shear stress plot in FIG. 2D, where the dashed line indicates the onset of shear thickening for fiber volume fractions φ<0.2 to be at a shear stress of 0.1±0.05 Pa; shear thickening, without any initial shear thinning, occurred for suspensions with φ>0.2. The trend in the first normal stress difference is similar to that of the viscosity for our suspensions, i.e., as soon the suspension is in the shear thickening regime, the first normal stress difference starts to increase with increasing shear rate, similar to the viscosity.

As a consequence of the significant viscoelasticity of the suspensions, which increased with fiber concentration, the suspensions were expelled from the parallel-plate gap in the rheometer, and climbed along the rotating plate, which is characteristic of the Weissenberg effect. Note that the measurements terminate at the shear rate at which fluid is expelled from the rheometer. This phenomenon is a signature of the onset of largely positive first normal stress differences in flows of flexible fiber suspensions.

Example 2A—Formation of Fiber Hydrogels

Flow-driven formation of fiber entanglements was performed for microfiber solutions having microfiber volume fractions of φ=0.1, 0.2 and 0.4. Nodes consisting of bent, entangled fibers increased with increasing fiber concentration and shear rate, thus creating within the suspension zones rich with entangled fibers and zones poor in fibers, such as those shown in FIG. 1C and described above. The formation of the hydrogels as described herein is unexpected. For example, known theories of dilute suspensions that have been developed to predict the onset of fiber deformation in fiber suspensions, including relating such predictions to bulk flow properties of fiber suspensions, such as normal stress differences, but such theories cannot be applied to the data herein reported. Additionally, other approaches to predict the flow behavior of dense fiber suspensions have established criteria that consider the number of contacts among fibers in a given volume. Yet, while such criteria can be used to estimate whether entanglements will form, they are unable to predict gel formation.

For the hydrogels formed according to the embodiments described herein, even in the case of concentrated suspensions of these microfibers, i.e. φ=0.4, the initial microfiber suspensions are observed to flow, as shown and described above for FIG. 1A. As such, the microfiber suspensions described herein can be poured and transferred as desired. However, when concentrated suspension of the microfibers were injected from a needle with an inner diameter of 0.21 mm, a hydrogel was unexpectedly and immediately extruded, and excess water as observed to be squeezed out of the network (as shown and described above for FIGS. 1B-1C). Microstructures of the extruded, dried hydrogels of Example 2A was observed to be random, creating a random microporous network.

Example 2B—Rheology of Fiber Hydrogels

Characterization of fiber entanglements was performed by shear flow rheometry. Although shear stress could represent part of the total stress involved during extrusion, shear rheology represents a clear method to investigate the process of entanglement formation and to demonstrate that our fiber suspensions can be converted into a hydrogel by using flow.

Example 2B-1—Measuring the Mechanical Properties of Fiber Hydrogels

Microfibers were produced using a microfluidic method known in the art, though the conventional approach disclosed herein is not limited to this fiber fabrication method (e.g., wet spinning, electrospinning, or any method that can produce very flexible high aspect ratio hydrophilic fibers). The microfibers were washed and concentrated to prepare high volume fraction (φ=0.4) suspensions, which can then be injected through a needle to produce a hydrogel. Also systematically studied was the shear rheology of the fiber suspensions in order to better understand the process of mechanical flocculation that occurs during shear, and which ultimately results in macroscopic gelation The geometry exploited in the rheology measurements reported here was a parallel plate with a diameter of 50 mm, a bottom plate roughness, Ra=4-7 µm, and a smooth upper plate. For the hydrogel, wall-slip did not play a role and hydrogel rheology could be performed with smooth plates.

Figure 3A:
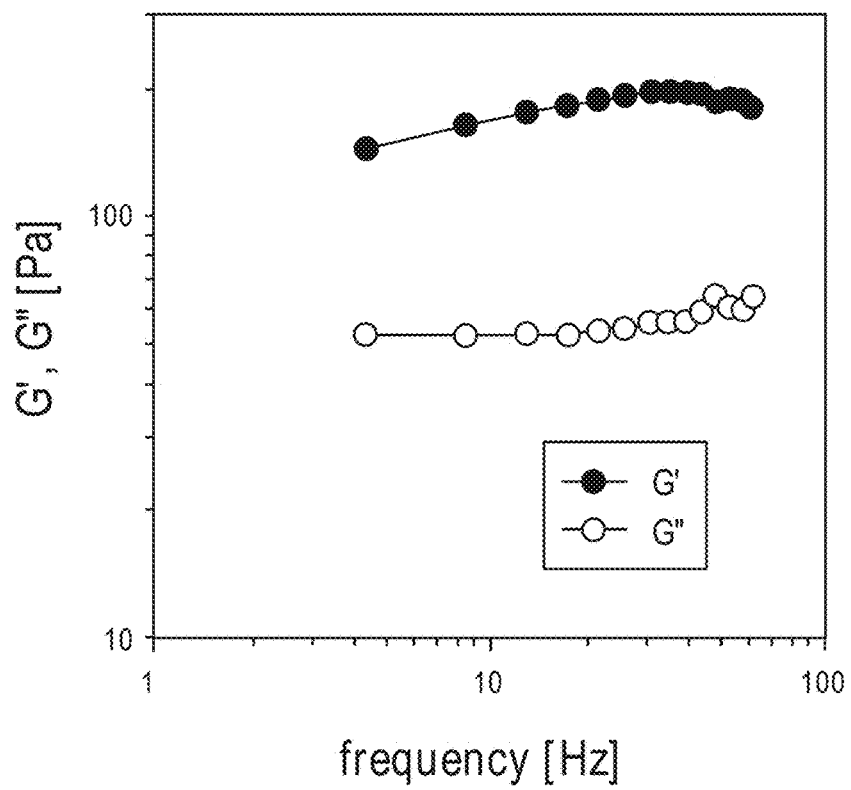
FIGS. 3A-3B are data plots showing the linear viscoelasticity plotted as a function of frequency of an exemplary extruded hydrogel of an embodiment, for a given stress of 1 Pa The elastic modulus, G', is shown by filled symbols and the viscous modulus, G", is shown by open symbols (FIG. 3A), and viscosity is plotted as a function of shear rate for a hydrogel (FIG. 3B).
Figure 3B:
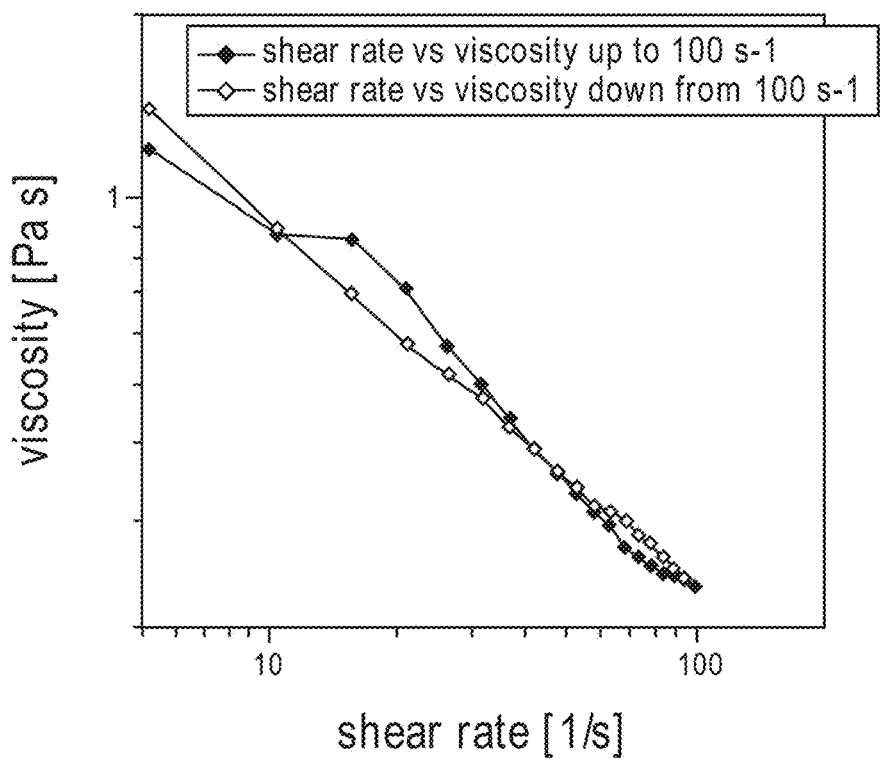

Once one has a concentrated suspension of flexible high aspect ratio hydrophilic fibers, it is possible to achieve flow induced gelation of the suspension if the appropriate stresses are applied to the suspension. Formation of a hydrogel was confirmed by measuring the shear moduli with a rheometer by applying a small oscillatory stress at different frequencies. The extruded material exhibited typical viscoelastic properties of a hydrogel, with the shear elastic modulus, G', greater than the viscous modulus, G" as shown in FIG. 3A. Meanwhile, viscosity plotted as a function of shear rate for a hydrogel produced from a suspension at $\phi=0.4$ in the graph of FIG. 3B shows that the hydrogel is a shear thinning material. It is noted that the material showed a full recovery of its initial viscosity once the shear rate was decreased back to the lowest value. Such a property permits the extruded hydrogel material to be easily spread over the site of application and once the stress is removed, an increased viscosity of the material "locks" the hydrogel onto the site, thereby avoiding sliding/leakage.

Figure 4A:
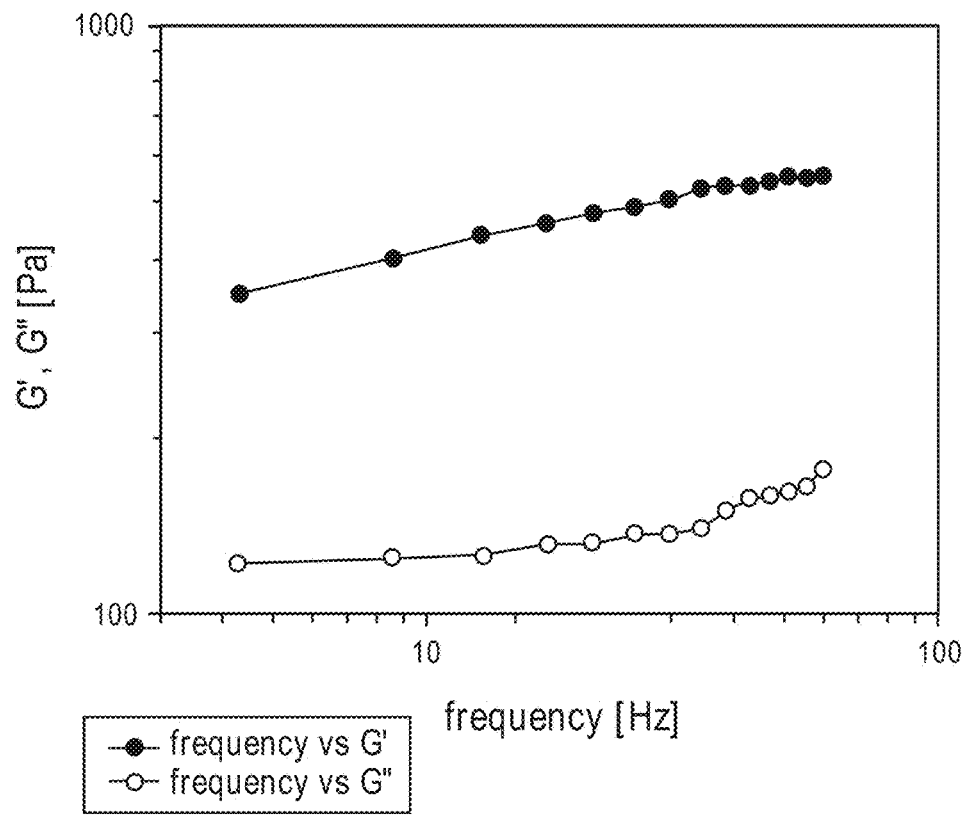
FIGS. 4A-4B are data plots showing linear viscoelasticity as a function of frequency of four fiber hydrogels samples produced from fiber suspensions having fiber volume fractions of ϕ=0.4, for a given stress of 1 Pa. The elastic modulus, G', is shown by filled symbols and the viscous modulus, G", is shown by open symbols.
Figure 4B:
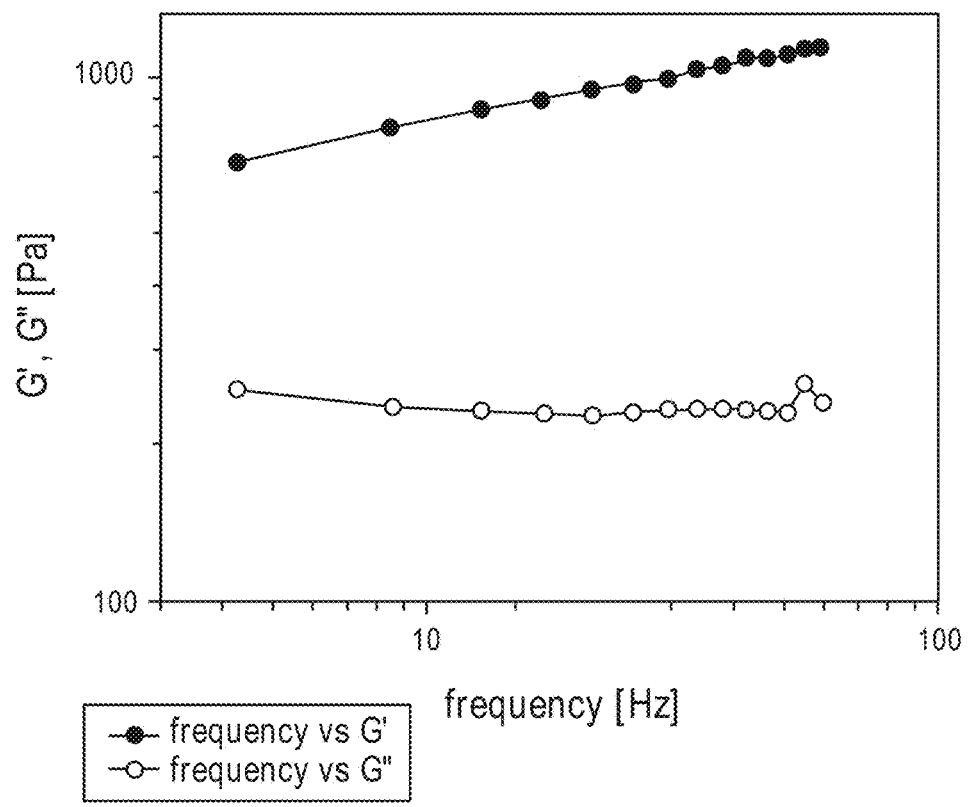
Figure 5A:
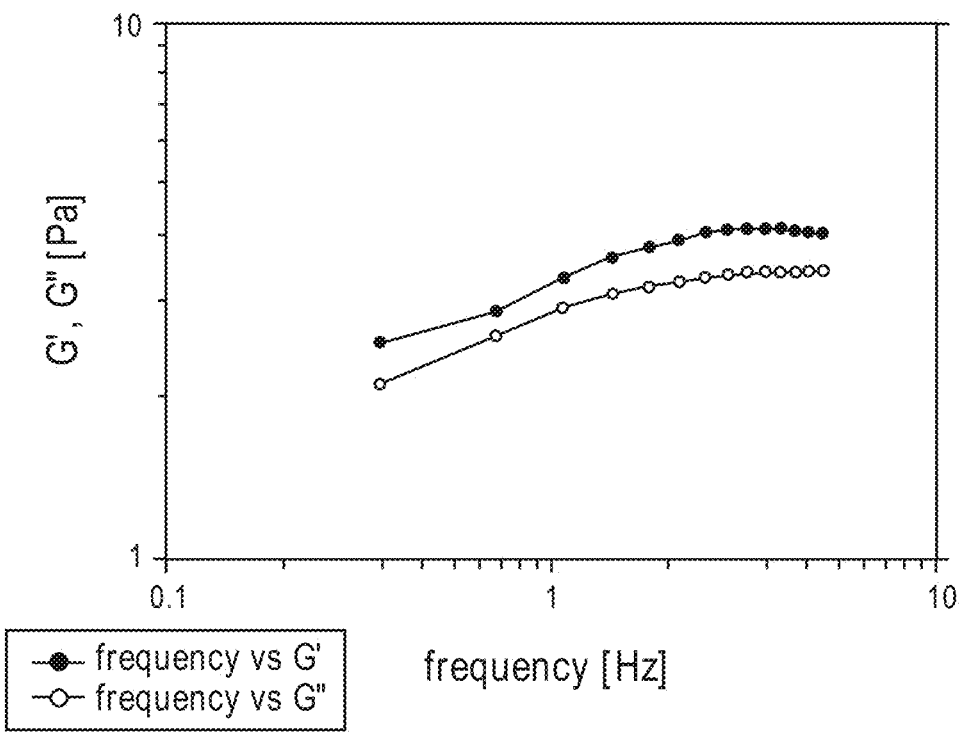
FIGS. 5A-5D are data plots showing linear viscoelasticity as a function of frequency of four fiber hydrogels samples produced from fiber suspensions having fiber volume fractions of ϕ=0.1, for a given stress of 0.7 Pa. The elastic modulus, G', is shown by filled symbols and the viscous modulus, G", is shown by open symbols.
Figure 5B:
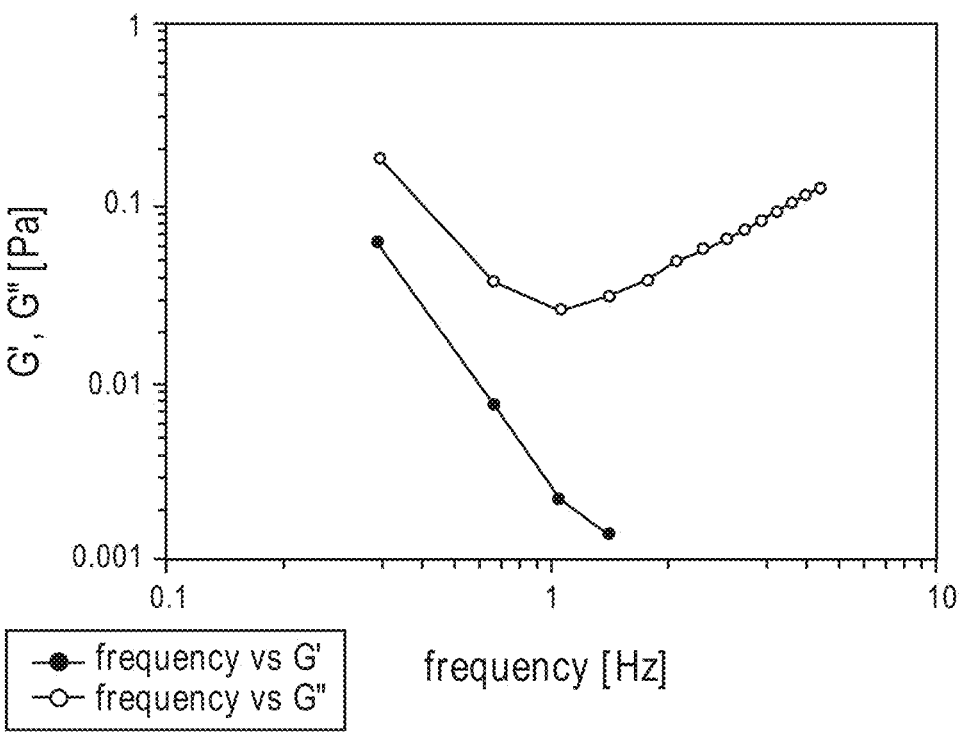
Figure 5C:
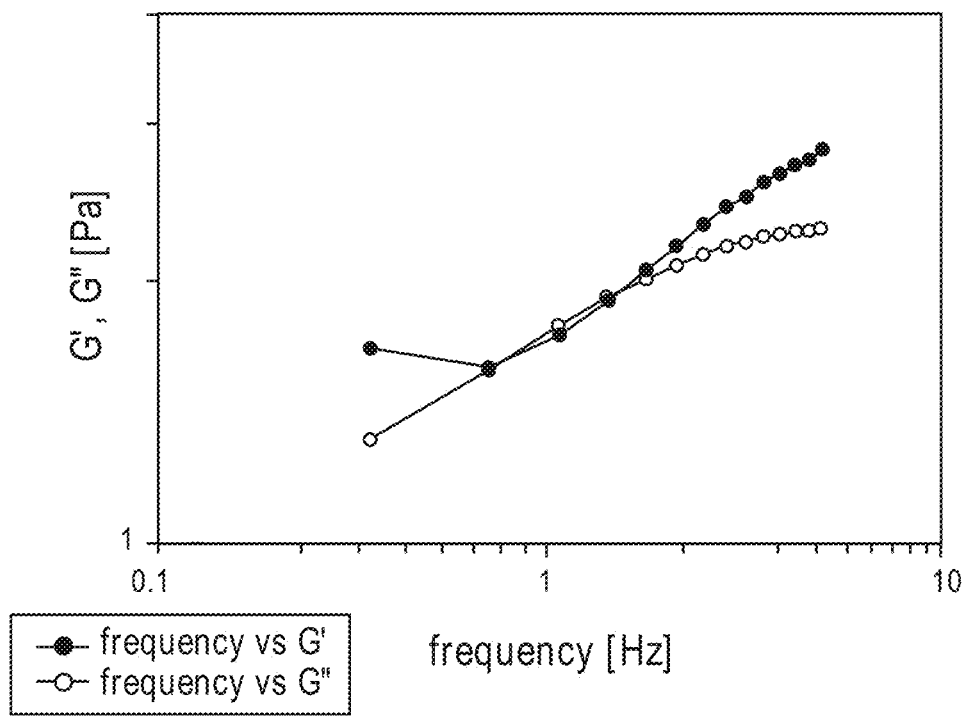
Figure 5D:
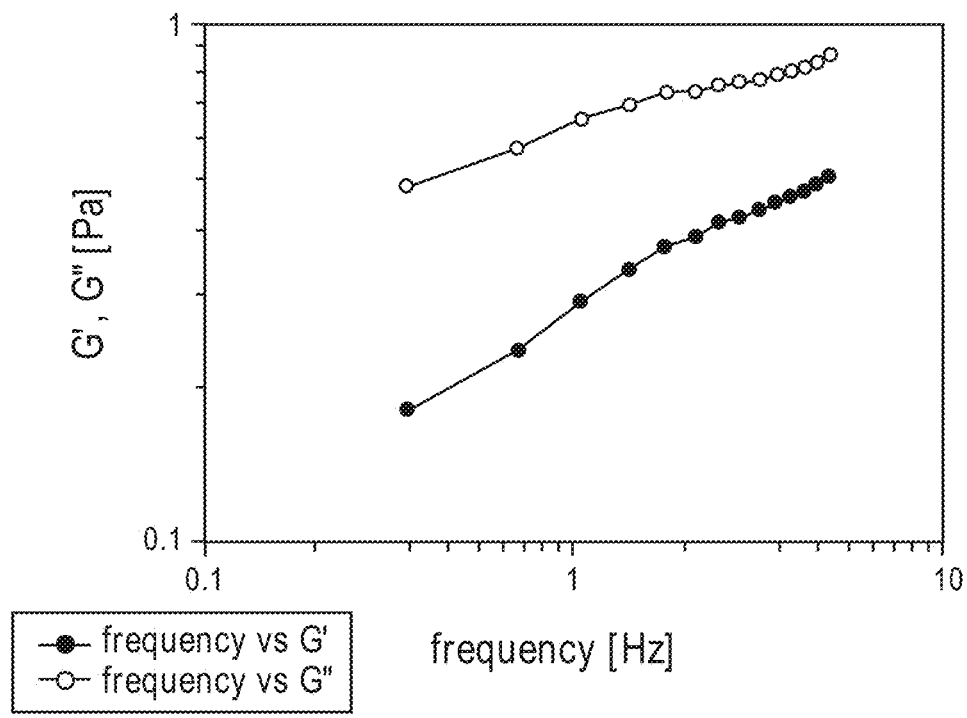

For hydrogels produced from extruding suspension with $\phi=0.4$, variability in the value of G' was observed among the different samples analyzed, with G' ranging from approximately 150 Pa to 1000 Pa. Also, some samples exhibited frequency dependent G' behavior. While not limited to any particular theory, it is believed that such sample to sample variability was due to the pre-stress that was applied to the material when loaded into the instrument. Moreover, a certain amount of water was always present in the extruded hydrogel, contributing to the variability in the elastic modulus of the samples. Nonetheless, rheological behavior that is typical of a hydrogel was observed as shown in FIGS. 4A-4B.

Figure 6A:
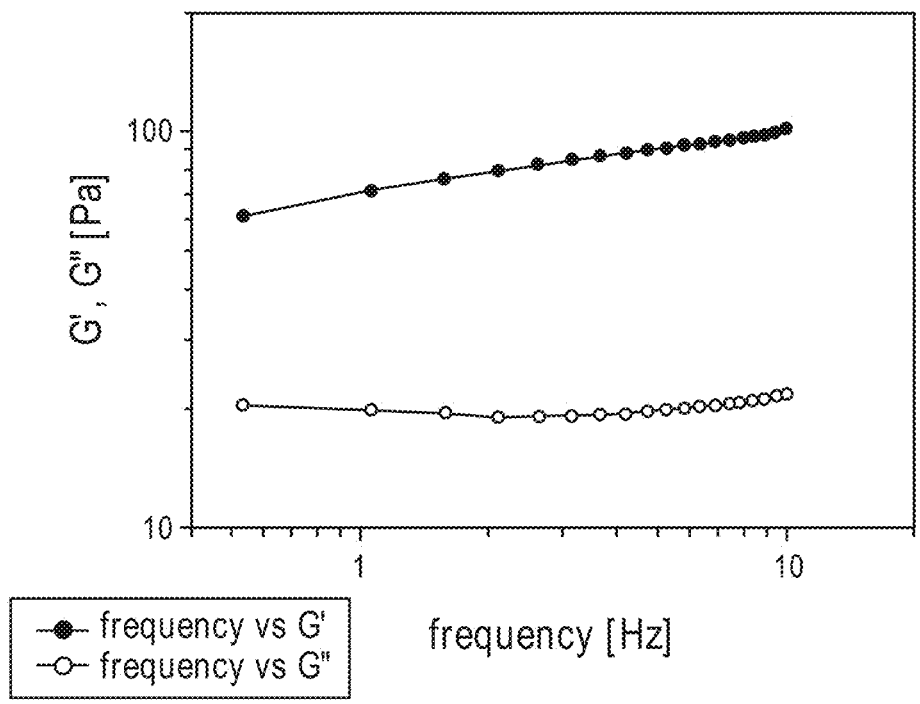
FIGS. 6A-6B are data plots showing linear viscoelasticity as a function of frequency of four fiber hydrogels samples produced from fiber suspensions having fiber volume fractions of ϕ=0.2, for a given stress of 0.7 Pa. The elastic modulus, G', is shown by filled symbols and the viscous modulus, G", is shown by open symbols.
Figure 6B:
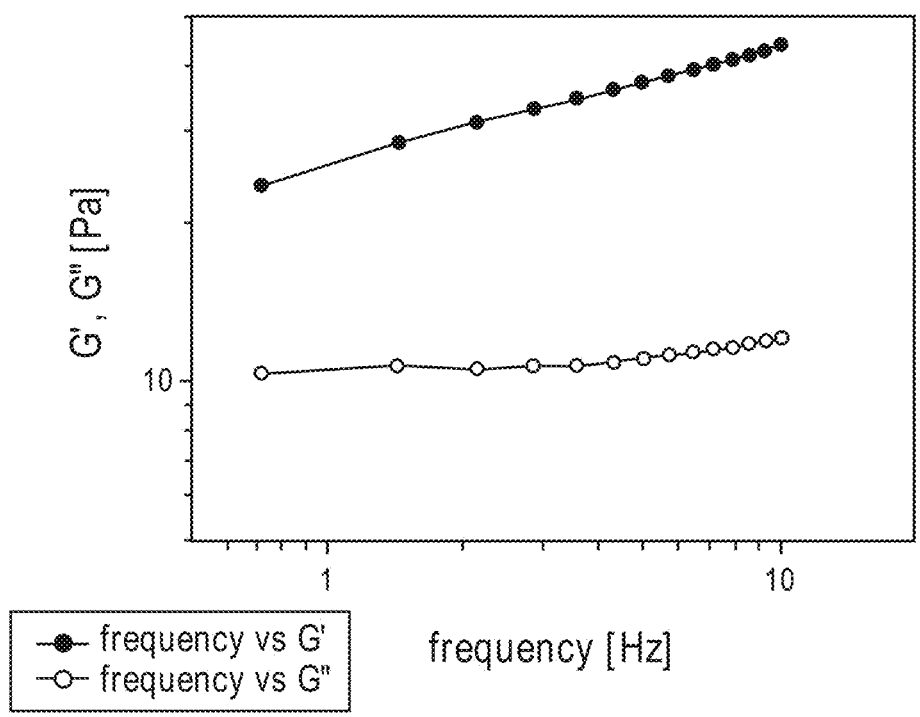
Figure 7A:
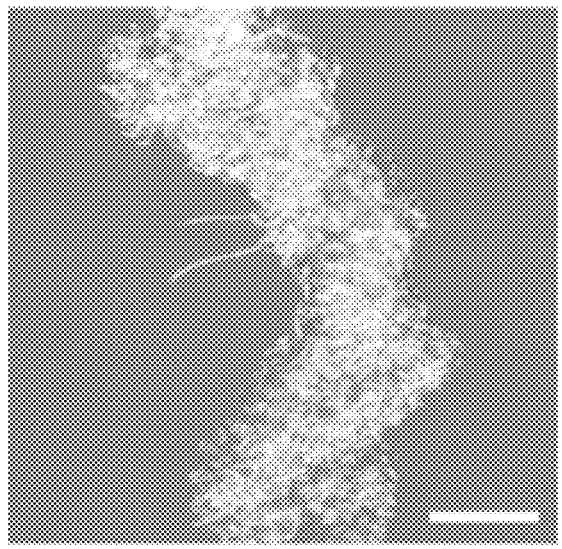
FIGS. 7A-7B are images illustrating swelling properties of extruded hydrogels of the embodiments.
Figure 7B:
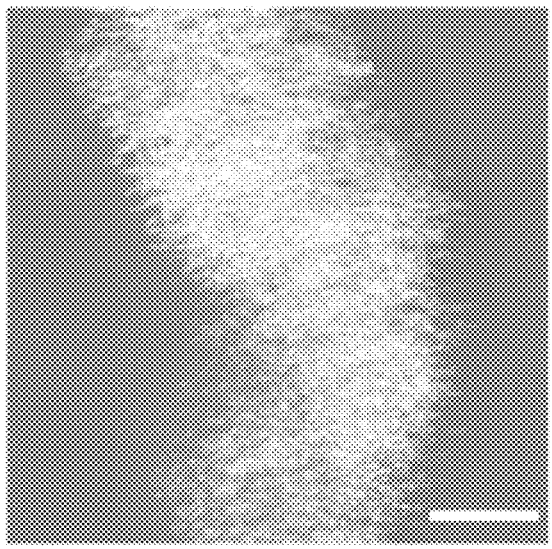
Figure 7C:
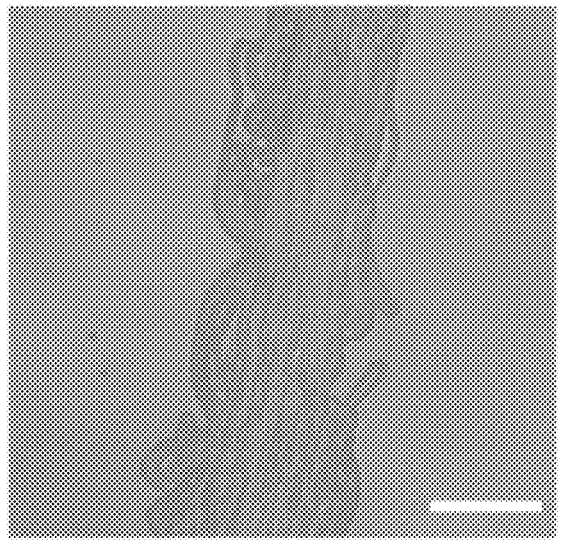
FIGS. 7C-7D are zoomed in images illustrating the swelling properties of extruded hydrogels of FIGS. 7A-7B.
Figure 7D:
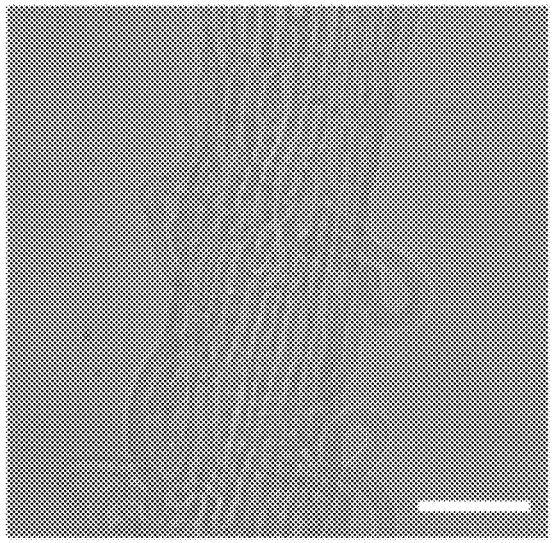

Example 2B-2—Effect of Microfiber Concentration in Suspensions on the Mechanical Properties of Fiber Hydrogels Formed Therefrom Rheological properties of hydrogels produced from extruding suspensions with different volume fractions of fibers ($\phi=0.1$, 0.2 and 0.4) were investigated. The hydrogel modulus was found to be concentration dependent. At $\phi=0.1$, the fiber suspensions did not produce hydrogels reproducibly (if a hydrogel formed, it was very weak, i.e. G' comparable to G" and not larger than a few Pascals), and the hydrogel properties were observed to be highly dependent on the injection/extrusion process and the remaining water content. The lack of reproducibility for hydrogels formed from suspensions having fiber volume fraction of $\phi=0.1$ are shown across the results in FIGS. 5A-5D. In contrast, for $\phi=0.2$, hydrogels were produced in a reproducible manner having, on average, a lower G' than those produced from suspensions with $\phi=0.4$ as observed across the results in FIGS. 6A-6B.

The modulus of the fiber hydrogel was observed to depend on the concentration of fibers in the initial suspension. When the fiber suspension was extruded, the product reproducibly exhibited the mechanical properties of a hydrogel when the fiber volume fraction of the initial suspension was at least $\phi=0.2$, and G' increased as $\phi$ increased from 0.2 to 0.4. In addition, the fiber hydrogels, which are obtained from extrusion from a needle and syringe, exhibit shear thinning behavior as well as complete viscosity recovery once the applied stress is removed. This feature permits the hydrogel material to be easily spread over the site of application and once the stress has been removed, the increased viscosity locks the hydrogel onto the site avoiding any possible sliding or leakage.

While the present teachings have been illustrated with respect to one or more implementations, alterations and/or modifications may be made to the illustrated examples without departing from the spirit and scope of the appended claims. For example, it will be appreciated that while the process is described as a series of acts or events, the present teachings are not limited by the ordering of such acts or events. Some acts may occur in different orders and/or concurrently with other acts or events apart from those described herein. Also, not all process stages may be required to implement a methodology in accordance with one or more aspects or embodiments of the present teachings. It will be appreciated that structural components and/or processing stages may be added or existing structural components and/or processing stages may be removed or modified.

Further, one or more of the acts depicted herein may be carried out in one or more separate acts and/or phases. Furthermore, to the extent that the terms "including," "includes," "having," "has," "with," or variants thereof are used in either the detailed description and the claims, such terms are intended to be inclusive in a manner similar to the term "comprising." The term "at least one of" is used to mean one or more of the listed items may be selected. As used herein, the phrase "one or more of", for example, A, B, and C means any of the following: either A, B, or C alone; or combinations of two, such as A and B, B and C, and A and C; or combinations of three A, B and C.

The term "about" indicates that the value listed may be somewhat altered, as long as the alteration does not result in nonconformance of the process or structure to the illustrated embodiment. Finally, "exemplary" indicates the description is used as an example, rather than implying that it is an ideal.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:
1. A hydrogel composition, comprising:
 a hydrogel consisting of;
  a liquid; and
  a plurality of stress induced physically entangled and mechanically interlocked microfibers forming a porous entangled network disposed in the liquid,
  wherein each of the plurality of stress induced physically entangled and mechanically interlocked microfibers can optionally include a charged group that is functionalized, and
 wherein the plurality of stress induced physically entangled and mechanically interlocked microfibers comprise a diameter in a range from about 0.5 µm to about 1500 µm.
2. The hydrogel composition of claim 1, wherein the plurality of microfibers each comprise an aspect ratio of about 200 to about 10,000, wherein a length of the microfibers is greater than a diameter of the microfibers.

3. The hydrogel composition of claim 1, wherein each of the plurality of microfibers comprise lengths in a range of from about 1 mm to about 50 mm.

4. The hydrogel composition of claim 1, wherein the liquid comprises one or more of a polymer solution, a surfactant, a solute, or combinations thereof.

5. The hydrogel composition of claim 1, wherein each of the plurality of microfibers comprise poly(ethylene glycol) diacrylate (PEG-DA).

6. The hydrogel composition of claim 1, wherein each of the plurality of microfibers comprise a maximum effective stiffness ($S^{eff}$) of from about $10^{-6}$ to about $10^{-3}$ as calculated by, $$S^{eff} = \frac{E_Y \pi D^4}{64 \eta_m \dot{\gamma} L^4}$$

where $E_y$ is Young's modulus, L is fiber length, D is fiber diameter, $\eta_m$, is a viscosity of a flowable suspension prior to shear flow to physically entangle the microfibers, and $\dot{\gamma}$ is a shear rate.

7. The hydrogel composition of claim 6, wherein the plurality of microfibers encapsulate a cargo.

8. The hydrogel composition of claim 7, wherein the cargo comprises one or more of therapeutics, biological materials, or sensing materials.

9. The hydrogel composition of claim 1, wherein the plurality of microfibers are hydrophilic microfibers.

10. The hydrogel composition of claim 1, wherein the plurality of fibers are functionalized with at least one protein.

11. The hydrogel composition of claim 1, wherein the liquid comprises a polymer aqueous solution comprising poly(ethylene glycol).

12. The hydrogel composition of claim 1, wherein a concentration of fibers in the hydrogel comprises a fiber volume fraction in a range of from about $\phi=0.4$ to about $\phi=0.8$.

13. A hydrogel composition, comprising:
a hydrogel consisting of:
a liquid; and
a plurality of stress induced physically entangled and mechanically interlocked microfibers forming a porous entangled network disposed in the liquid,
wherein the plurality of stress induced physically entangled and mechanically interlocked microfibers comprise a diameter in a range from about 0.5 μm to about 1500 μm, and
wherein the plurality of stress induced physically entangled and mechanically interlocked microfibers are hydrophilic.

14. The hydrogel composition of claim 1, wherein a modulus of the hydrogel is related to a concentration of a plurality of microfibers prior to entanglement by stress induced from the pressure-driven flow.

15. The hydrogel corn position of claim 13 wherein the plurality of microfibers each comprise an aspect ratio of about 200 to about 10,000, wherein a length of the microfibers is greater than a diameter of the microfibers.

16. The hydrogel composition of claim 13, wherein each of the plurality of microfibers comprise lengths in a range of from about 1 mm to about 50 mm.

17. The hydrogel composition of claim 13, wherein the liquid comprises one or more of a polymer solution, a surfactant, a solute, or combinations thereof.

18. The hydrogel composition of claim 13, wherein each of the plurality of microfibers comprise poly(ethylene glycol) diacrylate (PEG-DA).

19. The hydrogel composition of claim 13, wherein each of the plurality of microfibers comprise a maximum effective stiffness ($S^{eff}$) of from about $10^{-6}$ to about $10^{-3}$ as calculated by, $$S^{eff} = \frac{E_Y \pi D^4}{64 \eta_m \dot{\gamma} L^4}$$

where $E_y$ is Young's modulus, L is fiber length, D is fiber diameter, $\eta_m$ is a viscosity of a flowable suspension prior to shear flow to physically entangle the microfibers, and $\dot{\gamma}$ is a shear rate.

20. The hydrogel composition of claim 13, wherein the plurality of microfibers encapsulate a cargo.

21. The hydrogel composition of claim 20, wherein the cargo comprises one or more of therapeutics, biological materials, or sensing materials.

* * * * *